United States Patent [19]

Watson et al.

[11] 3,951,127
[45] Apr. 20, 1976

[54] CONSTANT TEMPERATURE DEVICE
[75] Inventors: Susan Steves Watson; William Keith Ross Watson, both of San Diego, Calif.
[73] Assignee: Kay Laboratories, Inc., San Diego, Calif.
[22] Filed: Sept. 25, 1974
[21] Appl. No.: 509,261

Related U.S. Application Data
[63] Continuation of Ser. No. 374,406, June 28, 1973, abandoned.

[52] U.S. Cl. ............................... 126/206; 126/204; 126/263; 44/3 R; 5/284; 5/347; 252/70; 128/399; 128/403
[51] Int. Cl.² .......................... A61F 7/06; F24J 1/00
[58] Field of Search ........... 126/263, 204, 262, 205, 126/400, 206; 165/46; 62/530; 128/399, 403; 44/3 R, 3 A; 132/36.2 B; 5/347, 284; 252/70

[56] References Cited
UNITED STATES PATENTS

| 811,750 | 2/1906 | Spieske | 44/3 R |
|---|---|---|---|
| 1,502,744 | 7/1924 | Perrault | 126/263 |
| 1,656,366 | 1/1928 | Sterling et al. | 44/3 A |
| 1,679,432 | 8/1928 | Lyon | 44/3 R |
| 1,894,775 | 1/1933 | Levenson | 44/3 R |
| 2,157,169 | 5/1939 | Foster | 126/263 |
| 2,827,438 | 3/1958 | Broadley | 126/263 |
| 3,175,558 | 3/1965 | Caillouette | 126/263 |
| 3,223,081 | 12/1965 | Hunt | 126/263 |
| 3,475,239 | 10/1969 | Fearon et al. | 44/3 R |
| 3,536,058 | 10/1970 | Hearst | 126/263 |
| 3,550,578 | 2/1970 | Fearon | 126/263 |
| 3,854,156 | 12/1974 | Williams | 126/204 |

FOREIGN PATENTS OR APPLICATIONS

| 748,220 | 11/1953 | United Kingdom | 126/263 |
|---|---|---|---|
| 1,208,903 | 11/1958 | France | 126/263 |

OTHER PUBLICATIONS
The Journal of Bone and Joint Surgery, Vol. 34–A, No. 2, Apr. 1952, p. 4.

Primary Examiner—John J. Camby
Assistant Examiner—Henry C. Yuen
Attorney, Agent, or Firm—Ellsworth R. Roston

[57] ABSTRACT

A flexible container having a substantially planar configuration encloses a first chemical having characteristics for being supercooled to maintain a liquid state even at temperatures below its melting point. A second chemical can be mixed with the first chemical in the container to initiate the crystallization of the first chemical at the substantially constant temperature of the melting point of the first chemical. The container can be enclosed in an insulation envelope to moderate the temperature of the device. The first chemical may include sodium thiosulfate pentahydrate which provides a desirable constant temperature of 48° C. The second chemical may include sodium borate pentahydrate or sodium sulfite which provides the first chemical with a desirable sandy configuration during crystallization in the α pentahydrate form. The sodium borate pentahydrate or sodium sulfite goes into solution or chemically complexes with the sodium thiosulfate in a manner such that subsequent supercooling can be achieved. Recycling of the device can then be accomplished by releasing another portion of the second chemical into the container. The resulting constant temperature device is particularly effective for use as a warm baby mattress, a warm blanket, or a hot water bottle substitute.

37 Claims, 8 Drawing Figures

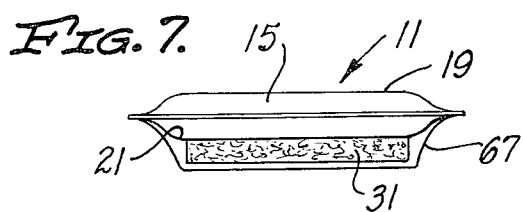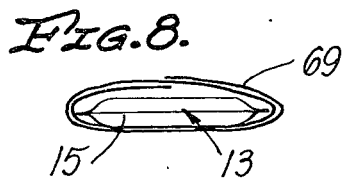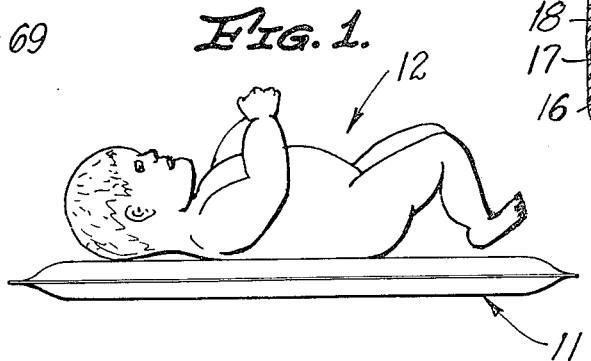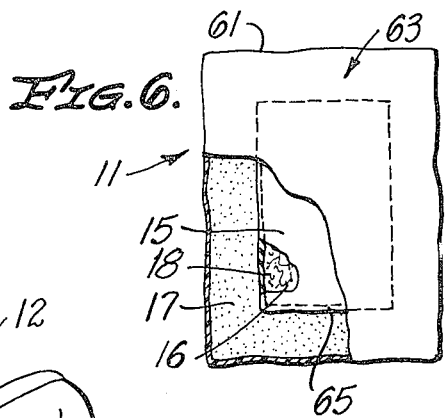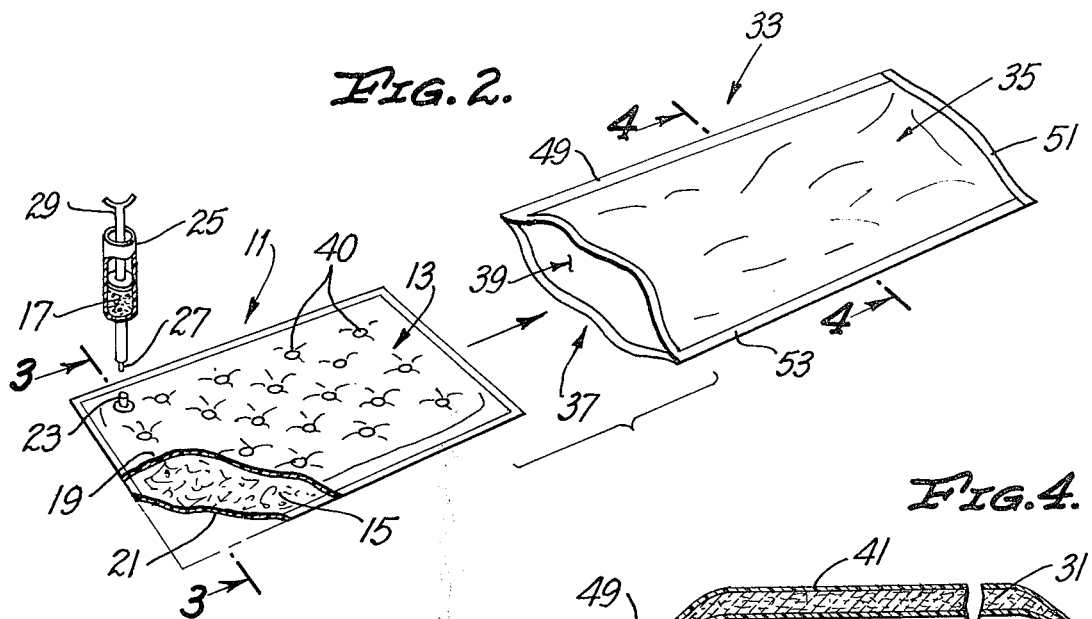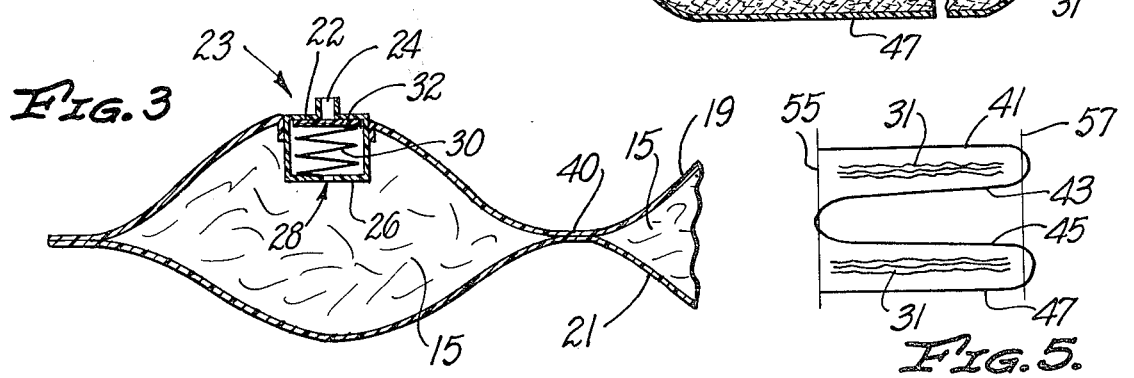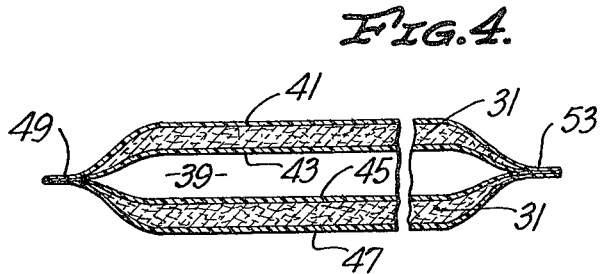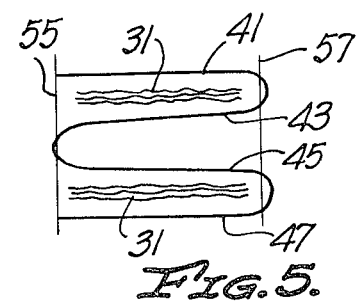

CONSTANT TEMPERATURE DEVICE

This is a continuation of application Ser. No. 374,406, filed June 28, 1973, now abandoned.

BACKGROUND OF THE INVENTION

1. Field of the Invention

The present invention relates generally to constant temperature devices, and more specifically to the use of chemical energy in such devices to provide a source of heat.

2. Description of the Prior Art

It is often desirable to increase the skin temperature of a person to provide an increase in comfort or blood circulation, or to aid in overcoming the adverse effects of shocks. Blankets have often been used in these situations to inhibit the flow of heat from a person to his environment. This type of blanket has not provided a source of heat, but rather has performed the function of an insulation so that the skin temperature of the person has only been slightly greater than its normal temperature.

To provide even higher skin temperatures, devices such as hot water bottles have been applied directly to the skin of the person to provide a source of heat. Since the effective period of use of the bottle has been directly related to the initial temperature of the water therein, these hot water bottles have either been initially uncomfortably hot, or their period of effective use has been relatively short. Furthermore, the temperature of the bottle has not remained constant over the effective period of its use so that initially it has been too hot and ultimately it has been too cold.

Heating pads and blankets including electrically energized coils have also been used to provide a source of heat. Typically, the coils have been energized through a thermostat, and delays inherent in the response of the device to the operation of the thermostat have caused significant fluctuations about a desired temperature.

Another type of heat source is a hydrocollator which is commonly used in physical therapy to provide a patient with a source of moist heat for an extended period of time. The hydrocollators of the prior art include canvas bags which are filled with sand and heated in boiling water. When the bag is sufficiently hot it is typically wrapped in a wet towel before application to the patient. Although these hydrocollators have been reusable, they have not provided a source of substantially constant temperature heat.

Other localized sources of heat have included a first container enclosing a first chemical such as calcium chloride. A second rupturable container has been disposed interiorly of the first container and has enclosed a second chemical having characteristics for exothemically reacting with the first chemical. These devices of the prior art have been particularly effective in providing a heat source of substantially constant temperature. Also, these devices have provided means for initiating the exothermic reaction by merely striking the first container to rupture the second container. Although these chemical devices of the prior art have been effective with respect to the hot water bottles and heating pads, it is always desirable to provide a constant temperature device which can be recycled to provide a source of heat at a subsequent controllable time.

SUMMARY OF THE INVENTION

In the present invention a substantially airtight container encloses a first chemical having characteristics for maintaining a liquid state at temperatures below its melting temperature. A second chemical can be injected into the container to provide a multiplicity of nucleation centers about which the first chemical crystallizes. Thus, the second chemical triggers a change of state of the first chemical, and this change of state occurs at the substantially constant temperature of the melting point of the first chemical.

The first chemical can include sodium thiosulfate pentahydrate which has a particularly desirable melting temperature of 48° C. The sodium thiosulfate pentahydrate can be stabilized with an impurity such as water, glycerin or urea so as to maintain its liquid state below its melting temperature. A basic chemical such as sodium hydroxide can be added to the first chemical to inhibit the growth of bacteria therein and to provide additional stability. The sodium thiosulfate pentahydrate is apparently capable of being crystallized into many different forms.

The first chemical can also include sodium acetate trihydrate individually or in combination with the sodium thiosulfite pentahydrate. In the latter case a eutectic compound is formed which has a melting point variable in accordance with the relative proportion of the sodium acetate trihydrate and sodium thiosulfate pentahydrate.

Sodium borate pentahydrate is particularly effective for use as the second chemical since it crystallizes the first chemical into a $\alpha$ pentahydrate form to provide a generally sandy configuration. A second chemical including sodium sulfite can also provide this desirable sandy configuration if the first chemical includes the sodium thiosulfate pentahydrate. This sandy texture can be particularly desirable if the device is to maintain contact with an irregular surface, such as the body of a human being.

The container can be formed from first and second face sheets which are heat-sealed at the edges thereof to provide a generally flat, airtight bag. The first and second face sheets can also be joined at points intermediate the edges of the container so that the flow of chemicals within the container is substantially inhibited.

The container can be disposed in an insulating envelope to maintain the surface temperature of the device in a range between 38°C and approximately 46°C. The insulating envelope is also desirable since it increases to approximately 6 to 8 hours the length of time over which the device provides a substantially constant temperature in a room temperature environment. The walls of the insulating envelope can be formed from vinyl and plyurethane foam which can be heated under pressure to provide the device with a sterile outer surface. The polyurethane foam is relatively spongy so that it functions both as a cushion and additionally as a heat insulator between the container and the object.

The device can be relatively small to facilitate its use in a localized area or it can be relatively large to augment its use as a blanket. As a blanket, the device not only insulates but also provides a source of heat which is particularly desirable for use with shock victims. The device of the present invention provides an excellent hydrocollator when wrapped in a wet towel. Not only is such a hydrocollator recyclable, but it also provides a source of substantially constant temperature heat.

A method associated with providing the recyclable constant temperature device includes the steps of heating the first chemical above its melting point and subsequently cooling the first chemical below its melting point while maintaining the liquid state of the first chemical. These and other features and advantages of the present invention will become more apparent with a description of the preferred embodiments taken in conjunction with the associated drawings.

DESCRIPTION OF THE DRAWINGS

FIG. 1 is a side elevational view of the constant temperature device of the present invention being used as a baby mattress;

FIG. 2 is an assembled perspective view of one embodiment of the device including a container and an insulation envelope;

FIG. 3 is a cross-sectional view of the container taken on line 3—3 of FIG. 2;

FIG. 4 is a cross-sectional view of the insulation envelope taken on line 4—4 of FIG. 2;

FIG. 5 is an expanded view of the insulation envelope shown in FIG. 4;

FIG. 6 is a plan view of an additional embodiment of the constant temperature device;

FIG. 7 is a side elevational view of still a further embodiment of the constant temperature device of the present invention; and FIG. 8 is a side elevational view of a hydrocollator including the constant temperature device of FIG. 2 wrapped in a wet towel to provide a source of moist heat.

DESCRIPTION OF PREFERRED EMBODIMENTS

A constant temperature device, which is designated generally by the reference numeral 11, is particularly adapted for use as a mattress for supporting a baby 12, as illustrated in FIG. 1. With reference to the assembled view of FIG. 2, it will be noted that one embodiment of the device 11 can include a container 13 of substantially any shape, and a first chemical 15 disposed interiorly of the container 13.

The first chemical 15 may include a chemical, compound, or any combination thereof having characteristics for supercooling to maintain a liquid state below its melting point. A second chemical 17 can be introduced into the container 13 to initiate the crystallization of the first chemical 15. This crystallization will typically take place over an extended period of time at the substantially constant temperature of the melting point of the first chemical 15. It follows that whether the device 11 is a hot or cold temperature device depends upon the melting point of the first chemical 15 and the temperature of the object, such as the baby 12, to which the device 11 is applied.

Although the container 13 can have generally any configuration, it may be desirable that it be relatively flexible so that it can conform to irregular shapes, such as elbows, knees and ankles. It may also be desirable that the container 13 have a generally planar configuration in order to maximize the surface area of the container 13. This flexible, planar configuration is particularly desirable when the device 11 is to be used as a baby mattress or a blanket. Under such circumstances, the container 13 may include a first face sheet 19 and a second face sheet 21. These face sheets 19 and 21 can be sealed at their edges to maintain the integrity of the container 13. It will be appreciated that the container 13 can also be formed from a single piece of sheet material bent back on itself to define both of the first and second face sheets 19 and 21, respectively.

In a preferred embodiment, the face sheets 19 and 21 are formed from vinyl. This material is particularly advantageous since the edges of the vinyl sheets 19 and 21 can be sealed under heat and pressure to impart airtight characteristics to the container 13. Vinyl is further desirable because it can be autoclaved to maintain the sterility of the container 13 and to recycle the chemical 15.

In a preferred embodiment, the sheets 19 and 21 are maintained in a contiguous relationship at a plurality of points 40 intermediate the edges of the face sheets 19 and 21. At these points 40, the face sheets 19 and 21 form barriers which inhibit the flow of the first chemical 15 within the container 13. This feature can be particularly desirable if any portion of the device 11 is to be used in a substantially vertical position. If the face sheets 19 and 21 are formed a vinyl material, the barriers can be formed by heat-sealing the face sheets at the points 40.

A valve 23 can be sealed in the first sheet 19 to provide a passage between the regions exterior and interior of the container 13. For example, the valve 23 can be a check valve having portions 22 defining an exterior orifice 24 and portions 26 defining an interior orifice 28. A spring 30 can be seated on the portions 26 to bias a diaphragm 32 against the portions 22. A ball valve could also be adapted for use as the valve 23.

The second chemical 17 can be introduced through the valve 23 by a syringe 25 having a nozzle 27 and a plunger 29. The nozzle 27 of the syringe 25 is adapted to snugly register with the portions 22 of the valve 23. As the plunger 29 is depressed the pressure on the diaphragm 32 resists the bias of the spring 30 and the second chemical 17 is forced through the orifice 28 into the container 13. Within the container 13, the first and second chemicals 15 and 17 mix to initiate the crystallization of the first chemical 15 at the substantially constant temperature of its melting point.

The ideal melting point for the first chemical 15 will depend upon the particular object, such as the baby 12, to which the device 11 is applied. For example, if the device 11 is to be used as a mattress for the baby 12, it is desirable that the melting point of the first chemical 15 be greater than the normal skin temperature of the baby 12 and less than a temperature which might have a tendency to inflame the skin of the baby 12.

Sodium thiosulfate pentahydrate, hereinafter referred to as hypo, has been found particularly adaptable for the first chemical 15 when the device 11 is intended to be used in proximity to the skin of a human being. Hypo has a melting point of substantially 48°C so that the device 11 will provide a substantially constant hot temperature in proximity to a human body which has a normal temperature of 37°C.

Hypo can be stabilized by an impurity 16, such as water, glycerin, or urea, to maintain a fluid state below the temperature of its melting point. As noted, these supercooled characteristics are particularly desirable for the first chemical 15. In a preferred embodiment of the device 11, the first chemical 15 includes 2-3 percent weight of water to stabilize the hypo. An additional percentage of the impurity can be added to the first chemical 15 if it is desirable to depress its melting point. For example, water can be added to the hypo in increasing percentages to provide the first chemical 15 with a melting point approaching 0° C.

It is also desirable that the first chemical 15 have a substantially large latent heat of fusion so that during a crystallization it can maintain its constant temperature for an extended period of time. Hypo has a latent heat of fusion of approximately 48 calories per gram which is relatively high for those chemicals having supercooled characteristics. In a preferred embodiment of the device 11, approximately 5 pounds of the hypo provides a substantially constant temperature of 48° C. for approximately 6 to 8 hours in a normal environment. Hypo is additionally advantageous for use in the first chemical 15 since it is nontoxic and non-irritating to the skin. Hypo can be crystallized apparently into different forms, one of which is a $\alpha$ pentahydrate form which provides the hypo with a generally sandy texture.

It may also be desirable that a chemical 18 to be added to the first chemical 15 in order to provide additional stability as well as raise the pH of the first chemical 15 in order to inhibit the growth of bacteria therein. Base compounds such as sodium hydroxide and sodium carbonate are particularly desirable for this purpose since they do not react with the hypo. In a preferred embodiment, sodium hydroxide is used in the ratio of 10 drops to 400 grams of the hypo to provide the first chemical 15 with a pH in the range of 9 to 10.

As noted, the hypo is particularly desirable for use as the first chemical 15 to provide the device 11 with a substantially constant temperature of 48°C. It should be noted, however, that other chemicals can be added to the hypo to provide other melting points. Other supercooled chemicals, such as sodium acetate trihydrate are particularly noteworthy since they maintain the supercooled characteristics of the first chemical 15. Hypo having a melting point of 48°C, and sodium acetate trihydrate having a melting point of 58°C, form a eutectic compound having a melting point in the range of 41°C to 48°C depending on their relative proportions in the first chemical 15. For example, a eutectic compound containing substantially 60% hypo and 40% sodium acetate trihydrate has a melting point of 42°C.

The second chemical 17 can be any chemical, compound or combination thereof preferably having a generally liquid configuration to augment its introduction through the valve 23 into the container 13. It is also desirable that the second chemical 17 have characteristics for triggering the crystallization of the first chemical 15 in order to liberate the latent heat of fusion of the first chemical 15 at the substantially constant temperature of its melting point. Sodium borate pentahydrate and sodium sulfite have been found particularly desirable for use as the second chemical 17 when the first chemical 15 includes hypo, since they crystallize the hypo into a $\alpha$ pentahydrate form providing a sandy texture. Sodium borate pentahydrate and sodium sulfite can be configured in a multiplicity of crystals typically having a maximum dimension of 10 microns. These crystals can be suspended in any inert fluid, such as the pure vegetable oils, including corn oil and peanut oil, to provide a generally fluid suspension. In a preferred embodiment, the sodium borate pentahydrate crystals are suspended in silicone oil, and a typical injection of the suspension includes 1 to 2 tenths of a milliliter.

The configuration of the first chemical 15 as it crystallizes can be particularly important if the device 11 is to be used in conjunction with an irregular surface. For example, if the device 11 is to be used as a baby mattress, or as a blanket, it is particularly desirable that the first chemical 15 not form a single rock or any sharp, point crystals during its crystallization. The choice of a second chemical 17 can be particularly important in providing the first chemical 15 with the desired configuration during crystallization. Thus, although several chemicals may be capable of triggering the first chemical 15, they may not all provide the desired configuration during its crystallization.

As previously mentioned, the sodium borate pentahydrate and sodium sulfite crystals have been desirable for the second chemical 17 since they provide the first chemical 15 including hypo with a generally granular, sandy configuration during crystallization. This can be explained generally by noting that each of these crystals of the second chemical 17 provides a nucleation center about which the hypo forms a $\alpha$ pentahydrate crystal. These small hypo crystals do not have particularly sharp edges and therefore have properties for generally fluid movement with respect to the other hypo crystals.

As noted, the supercooled chemicals are particularly desirable for use as the first chemical 15 since they can be triggered to provide heat having a substantially constant temperature. They are also desirable for a further reason. If the supercooled chemicals are heated to a temperature above their melting point to form a liquid, they will typically maintain the liquid state even after they are cooled to temperatures below their melting point. Furthermore, the supercooled chemicals will continue to maintain the liquid state until they are triggered by a subsequent addition of the second chemical 17 to the container 13. Thus, the supercooled chemicals enable the device 11 of FIG. 2 to be recycled so that a single device 11 of this embodiment can be used many times.

When the device 11 is reheated to liquify the first chemical 15, the sodium borate pentahydrate or sodium sulfite crystals which previously have been injected into the container 13, may go into solution or chemically complex with the first chemical 15. In such a case, the first chemical 15 is not retriggered by these crystals. This is particularly advantageous to the present invention since the first chemical 15 can be repeatedly supercooled and reinjected with the second chemical 17 to provide the constant temperature.

Since the second chemical 17 goes into solution or chemically complexes with the first chemical 15, it follows that the primary change occurring to the device 11 as a result of subsequent uses thereof, is an increase in the total volume of the chemicals in the container 13. This increase, of course, results from the repeated injections of the second chemical 17. Thus, the size of the container 13, the volume of the first chemical 15, and the injection volume of the second chemical 17, are primarily the conditions which affect the number of times the device 11 can be recycled and retriggered to provide the constant temperature.

In a preferred method for recycling the first chemical 15, the container 13 can be placed into an environment having a temperature higher than the melting point of the first chemical 15. For example, the container 13 can be placed in an autoclave so that as the container 13 is sterilized, the first chemical 15 is automatically recylced to its liquid state. The container 13 can then be cooled to a temperature below its melting point while the liquid state of the first chemical 15 is maintained. In the preferred embodiment of the device 11, this cooling temperature is substantially room temperature so that the cooling takes place automatically upon removal of the container 13 from the heated environment such as the autoclave. With the first chemical 15 in a liquid state below its melting point, this recyclable embodiment of the device 11 is prepared to subsequently provide a source of substantially constant temperature upon receipt of another injection of the second chemical 17.

A disposable embodiment of the device 11 can be constructed as illustrated in FIG. 6. In this embodiment, the second chemical 17 is preferably disposed in an outer, airtight container 61 similar to the container 13. The container 61 can also enclose an inner, rupturable container 63 having a rupturable seal 65 and, at least initially, containing the first chemical 15. Such a device including a rupturable inner container disposed in an outer container is disclosed and claimed in U.S. Pat. No. 3,674,134 entitled RUPTURABLE CONTAINER, issued on July 4, 1972, and assigned of record to the assignee of record of the present application.

In this particular embodiment of the device 11, the supercooled first chemical 15 can be released into the outer bag 61 by rupturing the seal 65. This will enable the second chemical 17 to trigger the first chemical 15 so that its latent heat of fusion is released at the substantially constant temperature of its melting point. The seal 65 is typically ruptured by striking the outer bag 61 so that the pressure of the first chemical 15 ruptures the seal 65. This disposable embodiment of the device 11 can be advantageously discarded after the first chemical 15 is entirely crystallized.

The outside surface temperature of both the recyclable and disposable embodiments of the invention can be moderated by placing insulation 31 around the device 11. As illustrated in FIGS. 2 and 4, the insulation 31 can be formed into the shape of an envelope 33 having first and second walls 35 and 37, respectively, which define an opening 39 and substantially enclose the container 13. In a preferred embodiment, the first wall 35 is formed from first and second face sheets 41 and 43, respectively, which are sealed at their coextensive edges to enclose a portion of the insulation 31. Similarly, the second wall 37 can include face sheets 45 and 47 which are sealed at their edges to enclose a portion of the insulation 31.

The first and second walls 35 and 37, respectively, can be joined along all but at least one of their edges to provide a plurality of seals 49, 51 and 53. Along at least the one edge, the walls 35 and 37 are preferably not joined so that they define the opening 39.

It will be appreciated by those skilled in the art that the face sheets 41, 43, 45 and 47 can be formed from a single sheet 55 as shown in FIG. 5. The sheet 55 can be repeatedly bent back on itself to define the face sheets 41, 43, 45 and 47; and the seals 49 and 53 can be formed along the lines 55 and 57, respectively.

In a preferred embodiment, the face sheets 41, 43, 45 and 47 are formed from vinyl and the edges of the face sheets are sealed by fusion under heat and pressure. The insulation 31 can comprise any of the polyurethane foams commonly available. These materials are particularly desirable since they can be autoclaved to maintain the sterility of the envelope 33. This particular embodiment of the envelope 33 when used in conjunction with hypo provides a temperature on the exterior surface of the envelope 33 of substantially 42°C which makes the device 11 particularly suitable for use in contact with the skin of the baby 12 or any other human being. The insulation 31, such as polyurethane foam, has a generally spongy configuration so that the envelope 33 acts as a cushion between the container 13 and the object such as the baby 12. Other insulations will be obvious to those of skill in the art to provide other temperatures on the exterior surface of the envelope 33. It will also be apparent that the temperature on the exterior surface of the envelope 33 will depend on the melting point of the first chemical 15. As noted, these melting points may vary in a range including the preferred temperatures between 41°C and 48°C. For example, if the first chemical 15 has a melting temperature of 41°C, the temperature on the exterior surface of the envelope 33 may be 35°C. Exterior surface temperatures in a preferred range between 35°C and 42°C can be achieved by providing the first chemical 15 with melting points between 41°C and 48°C in the manner previously discussed.

An additional embodiment of the invention is illustrated in FIG. 7. In this embodiment, the container 13 is formed with one of its walls including the face sheet 21, a sheet of the insulation 31, and an outer skin sheet 67. The outer skin sheet 67 can be formed from vinyl to facilitate heat sealing the sheets 21 and 67 along their peripheral edges with the insulation 31 sandwiched therebetween. The opposite wall of the container 13 may be similarly formed. On the other hand it may be desirable to leave the face sheet 19 uninsulated as shown in FIG. 7. This embodiment will permit rapid heat transfer through the face sheet 19 into the container 13 to facilitate fast recycling of the first chemical 15.

In still a further embodiment of the present invention, the device 11 is wrapped in a wet towel 69 to provide a hydrocollator as shown in FIG. 8. In the device 11 forming the hydrocollator it may be desirable that first chemical 15 have a higher melting point than those first chemicals 15 including hypo. If this is the case, the first chemical 15 may include only sodium acetate trihydrate which has a melting point of 58°C. This chemical can be triggered by the sodium borate pentahydrate to crystallize in the desirable hexagonal form. This hydrocollator is particularly advantageous since it is not only recyclable but also provides a source of moist heat which has a substantially constant temperature.

The recyclable constant temperature device 11 as described herein is particularly advantageous for use as a mattress for a baby, as a blanket for a shock victim, a hydrocollator, or as a hot water bottle substitute. Whereas the mattresses and blankets of the prior art have provided insulating characteristics, the device 11 can also provide a source of heat. Furthermore, this source of heat can be triggered at any time by merely injecting the second chemical 17 into the container 13. The temperature of the device 11 need not be thermostatically controlled since it automatically occurs at a substantially constant temperature of the melting point of the first chemical 15. Furthermore, the container 13 can be recycled so that the device 11 can be used repeatedly to provide its constant temperature over an extended period of time.

Sodium thiosulfate pentahydrate is particularly desirable for the first chemical 15 since it has a melting point of 48°C within a range of temperatures preferred for warm baby mattresses. The hypo can be stabilized in a liquid state below its melting point to provide the highly desirable supercooled characteristics. Also, the pH of the hypo can be raised to a preferred range to inhibit the growth of bacteria. The first chemical can also include sodium acetate trihydrate either individually or in combination with hypo.

The sodium borate pentahydrate and sodium sulfite are particularly desirable for the second chemical 17 since they are highly stable and can provide the first chemical 15 including hypo with a sandy texture during crystallization. These crystals go into solution when the device 11 is reheated so they do not retrigger the first chemical 15 prior to a second injection of the chemical 17.

Although the invention has been described with reference to particular embodiments and chemicals, it will be apparent to those skilled in the art that the invention can be otherwise embodied so that the scope of the invention should be ascertained only with reference to the following claims.

We claim:

1. In combination:
   an airtight container;
   a first chemical disposed interiorly of the container and having characteristics for being crystallized at a substantially constant melting temperature to generate heat and for providing a sandy texture when crystallized in a particular form, the first chemical having further characteristics for providing a liquid state when heated to a temperature greater than the melting temperature and for being supercooled to maintain the liquid state when cooled to a temperature less than the melting temperature, the first chemical being selected from a group including sodium thiosulfate pentahydrate and sodium acetate trihydrate; and
   means for introducing a second chemical to the first chemical interiorly of the container to initiate the crystallization of the first chemical in the supercooled state at the substantially constant melting temperature of the first chemical and in the α-pentahydrate crystalline form, the second chemical being selected from a group including sodium borate pentahydrate and sodium sulfite.

2. The combination recited in claim 1 wherein the sodium thiosulfate pentahydrate and the sodium acetate trihydrate in the first chemical are mixed in particular proportions to provide substantially a constant melting temperature of the first chemical at a particular temperature within a range between approximately 35° C and 48° C.

3. The combination recited in claim 2 wherein the first chemical includes sodium thiosulfate pentahydrate and sodium acetate trihydrate in a eutectic mixture for providing a melting temperature below the individual melting temperatures of sodium thiosulfate pentahydrate and sodium acetate trihydrate.

4. The combination recited in claim 3 wherein the first chemical includes at least 97% sodium thiosulfate pentahydrate and sodium acetate trihydrate and the remainder of the first chemical is an impurity selected from a group including water, glycerine and urea and having properties facilitating the maintenance of the liquid state of the sodium thiosulfate pentahydrate and sodium acetate trihydrate in the supercooled state.

5. The combination recited in claim 3 wherein the first chemical is a eutectic coumpound including about 60% sodium thiosulfate pentahydrate and about 40% sodium acetate trihydrate and having a melting temperature of approximately 42° C.

6. The combination set forth in claim 3 wherein the second chemical includes crystals of at least one of sodium borate pentahydrate and sodium sulfite and has properties of melting into a liquid state and of being mixed with the first chemical in the liquid state without materially affecting the melting temperature of the first chemical.

7. The combination set forth in claim 6 wherein the second chemical includes silicone oil having fluid properties for suspending the crystals of the second chemical to provide for an efficient introduction of the second chemical into the first chemical.

8. In combination:
   a container;
   a first chemical disposed interiorly of the container and having a particular melting temperature and properties of being supercooled at a liquid state below the particular melting temperature and of being retained in such liquid state at ambient temperatures and of being crystallized at the particular melting temperature into the α-pentahydrate form to provide a source of heat at a substantially constant temperature, the first chemical being selected from a group including sodium thiosulfate pentahydrate and sodium acetate trihydrate;
   first means disposed in the container for stabilizing the first chemical in a liquid state below the particular melting temperature of the first chemical; and
   second means introduced to the first chemical interiorly of the container for initiating the crystallization of the first chemical at the particular melting temperature into the crystals of the α-pentahydrate form, the second means being selected from a group including sodium borate pentahydrate and sodium sulfite.

9. The combination recited in claim 8 wherein injection means are provided to inject the second chemical into the first chemical and wherein the container includes:
   a first flexible face sheet; and
   a second flexible face sheet having edges sealed to the edges of the first face sheet to define for the container a substantially airtight cavity substantially filled with the first chemical and wherein the injection means includes:
   valve means contiguous with the first face sheet and providing a passage communicating between the container and the cavity for introducing the second means to the first chemical.

10. The combination set forth in claim 9 wherein the valve means comprises a check valve having portions which snugly register with the container to facilitate the introduction of the second means into the container.

11. The combination recited in claim 8 wherein the second means includes a multiplicity of crystals each providing a nucleation center about which a portion of the first chemical forms at least one crystal and wherein the first chemical is provided with properties to provide α-pentahydrate crystals.

12. In combination:
   a container;
   a first chemical disposed interiorly of the container and having a particular melting temperature in a range between approximately 38° C and 42° C and characteristics for maintaining a liquid state at temperatures below the particular melting temperature and being triggered to become crystallized at the particular melting temperature in an exothermic reaction, the first chemical being selected from a group including sodium thiosulfate pentahydrate and sodium acetate trihydrate;

a second chemical introduced into the container and having properties for initiating the crystallization of the first chemical in the liquid state bleow the particular melting temperature to give off a constant temperature heat at the particular melting temperature, the second chemical being selected from a group including sodium borate pentahydrate and sodium sulfite; and an envelope removably enclosing the container and having insulating characteristics for maintaining the exterior surface temperature of the envelope in the range between 38°C and 42°C.

13. The combination set forth in claim 12 wherein the envelope includes:
a first sheet defined by a plurality of edges;
a second sheet having a plurality of edges sealed to the edges of the first sheet to define a first cavity;
insulation means disposed in the first cavity and cooperative with the first and second sheets to form a first wall with the first and second sheets;
a third sheet defined by a plurality of edges;
a fourth sheet having edges sealed to the edges of the third sheet to define a second cavity;
insulation means disposed in the second cavity and cooperative with the third and fourth sheets to form a second wall with the third and fourth sheets;
the first wall being sealed to the second wall along all but at least one of the edges thereof to define the envelope; whereby
the container is insertable into the envelope and is removable from the envelope through an opening defined by the unsealed edges of the first and second walls.

14. The combination set forth in claim 12 further comprising first means disposed interiorly of the container and mixed with the first chemical for inhibiting the growth of bacteria in the first chemical.

15. The combination recited in claim 14 wherein the first means includes a third chemical selected from a group including sodium hydroxide and sodium carbonate and having basic properties for raising the pH of the first chemical to a range between 9 and 10 to inhibit the growth of bacteria.

16. The combination set forth in claim 12 further comprising a third chemical mixed with the first chemical interiorly of the container and having properties for stabilizing the first chemical in the supercooled state, the third chemical being selected from a group including water, glycerin and urea.

17. The combination set forth in claim 12 wherein the first chemical includes sodium thiosulfate pentahydrate and the second chemical includes sodium borate pentahydrate in a eutectic mixture for crystallizing at a temperature between approximately 38° C and 42° C.

18. The combination set forth in claim 17 wherein the sodium borate pentahydrate or the sodium sulfite is suspended in a silicone oil to facilitate the introduction of the sodium borate pentahydrate or the sodium sulfite into the first chemical for triggering the first chemical into a crystalline state and a small amount of water is mixed with the first chemical to stabilize the first chemical in the supercooled state.

19. The combination set forth in claim 18 further comprising a chemical selected from a group including sodium carbonate and sodium hydroxide mixed with the first chemical interiorly of the container, the chemical selected from the group including sodium carbonate and sodium hydroxide having properties for maintaining the first chemical at a Ph between 9 and 10 to inhibit the growth of bacteria.

20. A method for providing a recyclable constant temperature device, including the steps of:
providing a container;
enclosing in the container a first chemical having a particular melting temperature and characteristics for being supercooled to maintain a liquid state below the melting temperature and for being triggered at a controlled instant of time into a crystalline state of the $\alpha$-pentahydrate form to release heat at the particular temperature, the first chemical being selected from a group including sodium thiosulfate pentahydrate and sodium acetate trihydrate;
introducing a second chemical into the container to initiate the crystallization of the first chemical into the crystals with the sandy texture and to obtain the generation of heat for an extended period of time at the substantially constant temperature during such period of crystallization, the second chemical being selected from a group including sodium borate pentahydrate and sodium sulfite; and
recycling the first chemical to provide the first chemical in the liquid state so that the device can be used subsequently to provide a source of substantially constant temperature by crystallizing at the particular temperature into the crystals of the $\alpha$-pentahydrate form.

21. The combination set forth in claim 3 wherein the second chemical is disposed in a fluid suspension including silicone oil to facilitate the introduction of the second chemical into the first chemical and the triggering of the first chemical in the $\alpha$-pentahydrate form.

22. The combination set forth in claim 12 wherein the second chemical has properties of being retained in solution with the first chemical in the supercooled state of the first chemical without materially affecting the triggering of the first chemical into the crystalline state at the particular temperature.

23. The combination set forth in claim 12 wherein the second chemical has properties for chemically complexing with the first chemical so that the first chemical can be repeatedly supercooled at the particular temperature.

24. The combination set forth in claim 1 wherein the container includes a plurality of walls and at least a first one of the walls comprises:
a first sheet member having a first side and a second side, the first side being disposed in contiguous relationship with the first chemical;
a second sheet member sealed to the second side of the first sheet member to define a cavity between the first and second sheet members; and
insulation means disposed in the cavity in cooperative relationship with the first and second sheet members to inhibit the transfer of heat through the first wall of the container.

25. The combination recited in claim 24 wherein at least a second one of the walls of the container is devoid of insulation means to facilitate the transfer of heat through the second wall during the heating of the combination.

26. A hydrocollator adapted for application to a patient undergoing physical therapy and including:
   first means providing a source of heat at a substantially constant temperature, the first means including a supercooled material having properties of being crystallized into the α-pentahydrate form at the substantially constant temperature to generate heat and of providing a liquid state when heated to a temperature greater than the substantially constant temperature and of being supercooled to maintain the liquid state when cooled to a temperature less than the substantially constant temperature, the supercooled fluid being selected from a group including sodium acetate trihydrate and sodium thiosulfate pentahydrate, the supercooled fluid having properties of being triggered into the crystalline state of the α-pentahydrate form at the substantially constant temperature and of being retained in the liquid state at the substantially constant temperature;
   second means disposed between the first means and the patient for increasing the moisture content of the heat imparted to the patient by the first means at the substantially constant temperature by the crystallization of the supercooled material into the α-pentahydrate form; and
   third means for introducing a second chemical into the supercooled fluid to initiate the crystallization of the supercooled fluid at the substantially constant temperature in the α-pentahydrate form, the second chemical being selected from a group including sodium borate pentahydrate and sodium sulfite, the second chemical having properties of triggering the supercooled fluid into the crystalline form without affecting the temperature at which the supercooled fluid becomes subsequently converted into the liquid form and thereafter becomes triggered into the crystalline form.

27. The hydrocollator recited in claim 26 wherein the first means comprises:
   a container;
   the supercooled material being disposed in the container means; and
   means for introducing the second chemical to the supercooled material interiorly of the container to initiate the crystallization of the supercooled material at the substantially constant melting temperature of the supercooled material.

28. A method for providing a baby mattress, including the steps of:
   providing a first chemical having characteristics for melting at a particular temperature and for maintaining a liquid state even at temperatures below the particular temperature and for crystallizing at the particular temperature to liberate heat, the first chemical being selected from a group including sodium thiosulfate pentahydrate and sodium acetate trihydrate and having properties of crystallizing in a sandy texture at the particular temperature;
   retaining the first chemical in a container upon which the baby is to be disposed;
   heating the first chemical to a temperature greater than the melting point to impart a latent heat of fusion to the first chemical and thereby provide the first chemical with a liquid state even at temperatures below the particular temperature;
   cooling the first chemical to a temperature less than the particular temperature while retaining the latent heat of fusion in the first chemical, and thereby maintaining the first chemical in the liquid state;
   providing a second chemical having characteristics for being introduced to the first chemical in the liquid state and at a temperature below the particular temperature to trigger the crystallization of the first chemical at the particular temperature, the second chemical being selected from a group including sodium borate pentahydrate and sodium sulfite and having properties of triggering the first chemical at the particular temperature into the crystals with the sandy texture; and
   mixing a first portion of the second chemical with the first chemical in the liquid state and below the particular temperature to trigger the crystallization of the first chemical at the particular temperature into the crystals with the sandy texture and thereby release the latent heat of fusion at the substantially constant temperature and produce a crystallization of the first chemical in the sandy texture.

29. The method recited in claim 28 further comprising the steps of:
   heating the first chemical and the first portion of the second chemical to a temperature greater than the particular temperature to impart a second latent heat of fusion to the first chemical and thereby provide the first chemical with a liquid state;
   cooling the first chemical and the first portion of the second chemical to a temperature less than the particular temperature to recycle the first chemical and thereby provide the first chemical with a liquid state with the latent heat of fusion in the first chemical; and
   mixing a second portion of the second chemical with the recycled first chemical to retrigger the crystallization of the first chemical at the particular temperature into crystals with sandy texture and thereby release the second latent heat of fusion at the particular temperature and produce a crystallization of the first chemical in the sandy texture.

30. The method recited in claim 28 wherein the container retaining the first chemical is airtight and the mixing step includes the step of introducing the first portion of the second chemical into the airtight container to mix with the first chemical and to trigger the crystallization of the first chemical at the particular temperature into the crystals with the sandy texture to release the latent heat of fusion of the first chemical.

31. The method recited in claim 29 wherein the first and second portions of the second chemical are introduced into the container without interfering with airtight characteristics of the container.

32. The method recited in claim 31 wherein the second chemical has properties such that the introduction of the second chemical into the mixture with the first chemical does not affect the temperature at which the first chemical crystallizes.

33. The method recited in claim 28 wherein the first chemical includes sodium thiosulfate pentahydrate having a plurality of crystallization forms including a αpentahydrate form having a sandy configuration, and the second chemical has properties for triggering the crystallization of the first chemical in the α-pentahydrate form.

34. The method recited in claim 33 wherein the sodium thiosulfate pentahydrate and sodium acetate trihydrate are mixed in a eutectic mixture to melt into the liquid and be triggered into the crystalline at a temperature in the range of approximately 38° C to 42° C.

35. The combination recited in claim 8 wherein the first chemical is responsive to the second means to crystallize in a grainy structure and wherein the first chemical and the second means have properties of retaining the temperature of crystallization at a substantially constant value even upon multiple introductions of the second means into the first chemical.

36. The combination recited in claim 35 wherein the first chemical and the second means have properties to obtain a crystallization of the first chemical in the α-pentahydrate form and wherein the second means includes a plurality of crystals each providing a nucleation center about which the first chemical forms crystals in the α-pentahydrate form.

37. A method for providing a recyclable constant temperature device, including the steps of:
providing a container;
enclosing in the container a first chemical having properties of melting at a particular temperature and characteristics for being supercooled to maintain a liquid state below the particular temperature and characteristics for being triggered into the α-pentahydrate crystalline state at the particular temperature to obtain a release of heat, the first chemical being selected from a group including sodium thiosulfate pentahydrate and sodium acetate trihydrate;
introducing a second chemical into the container to initiate the crystallization of the first chemical into the α-pentahydrate crystalline state, the crystallization continuing for an extended period of time at the particular temperature, the second chemical having properties of being mixed with the first chemical without affecting the melting temperature of the first chemical, the second chemical being selected from a group including sodium borate pentahydrate and sodium sulfite;
recycling the first chemical and the second chemical in the liquid state at a temperature above the particular temperature so that the device can be used subsequently to provide a source of heat at the particular temperature;
subsequently cooling the first and second chemicals below the particular temperature while maintaining the liquid state of the first and second chemicals;
and introducing an additional amount of the second chemical into the container to trigger the first chemical into the α-pentahydrate crystallization state at the particular temperature.

* * * * *